United States Patent
Thoemmes et al.

(10) Patent No.: US 8,596,267 B2
(45) Date of Patent: Dec. 3, 2013

(54) INHALER

(75) Inventors: Ralf Thoemmes, Willich (DE); Jessica Frentzel-Beyme, Witten (DE); Jens Besseler, Dortmund (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 206 days.

(21) Appl. No.: 12/863,488

(22) PCT Filed: Jan. 23, 2009

(86) PCT No.: PCT/EP2009/000423
§ 371 (c)(1),
(2), (4) Date: Aug. 17, 2010

(87) PCT Pub. No.: WO2009/092592
PCT Pub. Date: Jul. 30, 2009

(65) Prior Publication Data
US 2011/0036350 A1   Feb. 17, 2011

(30) Foreign Application Priority Data
Jan. 24, 2008  (EP) .................................. 08001292

(51) Int. Cl.
*A61M 15/00*  (2006.01)
(52) U.S. Cl.
USPC ............ 128/203.21; 128/200.24; 128/203.12; 128/203.15; 128/205.23
(58) Field of Classification Search
None
See application file for complete search history.

(56) References Cited

U.S. PATENT DOCUMENTS

| | | | | |
|---|---|---|---|---|
| 5,590,645 A | * | 1/1997 | Davies et al. ............ | 128/203.15 |
| 7,225,808 B2 | * | 6/2007 | Davies et al. ............ | 128/203.15 |
| 2006/0196504 A1 | * | 9/2006 | Augustyn et al. ........ | 128/203.15 |
| 2006/0266842 A1 | | 11/2006 | Boggs | |
| 2007/0062525 A1 | * | 3/2007 | Bonney et al. ........... | 128/203.21 |
| 2007/0181123 A1 | | 8/2007 | Houzego | |
| 2008/0116220 A1 | | 5/2008 | Pocock et al. | |
| 2008/0196718 A1 | * | 8/2008 | Connell et al. .......... | 128/203.15 |
| 2008/0202515 A1 | * | 8/2008 | Hodson et al. .......... | 128/203.21 |
| 2010/0139654 A1 | | 6/2010 | Thoemmes et al. | |

FOREIGN PATENT DOCUMENTS

| | | |
|---|---|---|
| WO | 0205879 A1 | 1/2002 |
| WO | 03030974 A1 | 4/2003 |
| WO | 2005102430 A1 | 11/2005 |
| WO | 2006079750 A1 | 8/2006 |
| WO | 2006123110 A1 | 11/2006 |
| WO | 2007096111 A2 | 8/2007 |

OTHER PUBLICATIONS

International Search Report, form PCT/ISA/210, for corresponding PCT/EP2009/000423; date of mailing Apr. 6, 2009.

* cited by examiner

*Primary Examiner* — Loan Thanh
*Assistant Examiner* — Andrew S Lo
(74) *Attorney, Agent, or Firm* — Michael P. Morris; Mary-Ellen M. Devlin

(57) ABSTRACT

An inhaler (1) for delivery of a powder-form inhalation formulation from a blister strip (2) with a plurality of blister pockets (3) is proposed. A tape is used for numbering.

2 Claims, 4 Drawing Sheets

INHALER

Figure 1:
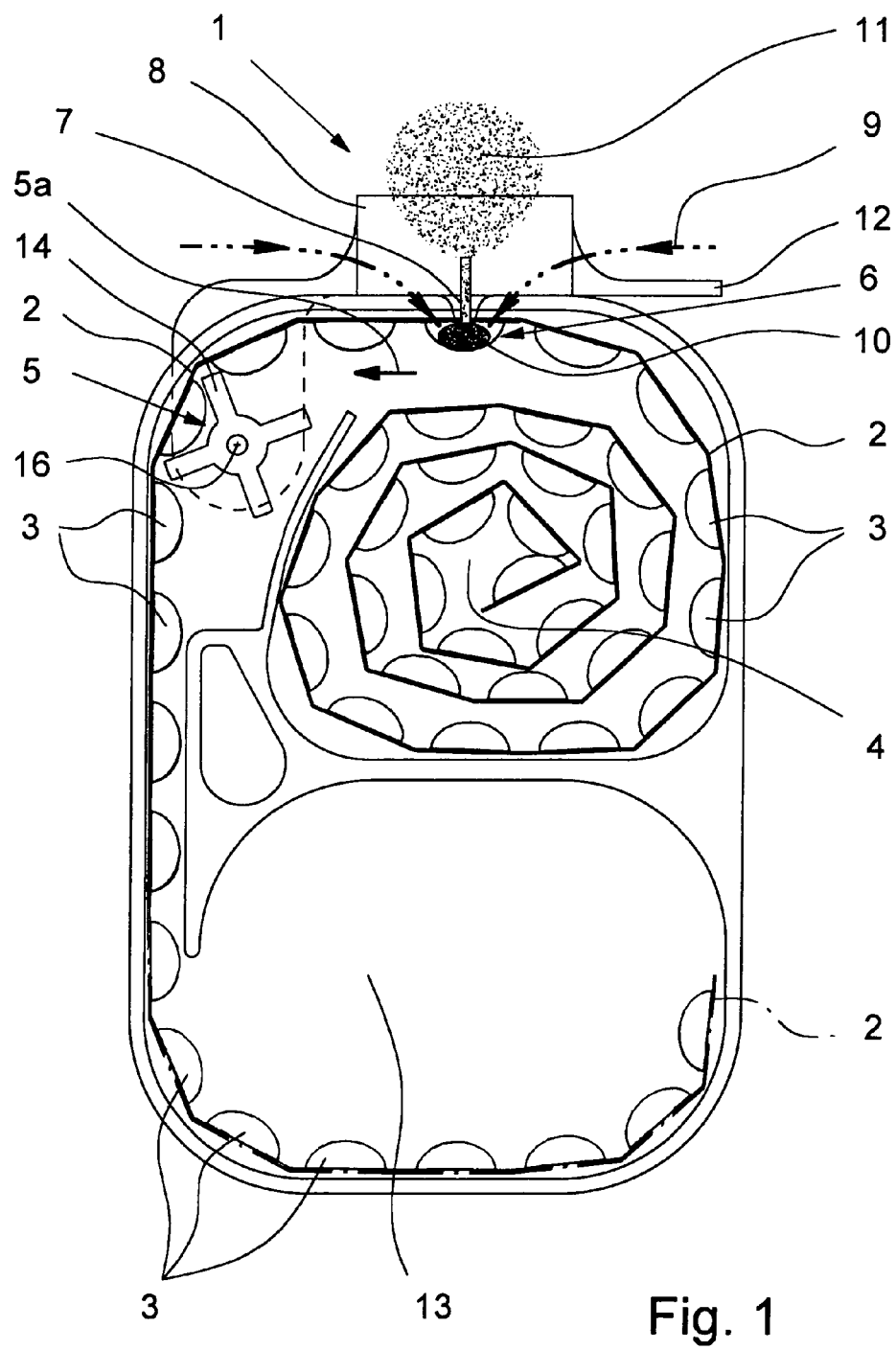

The present invention relates to an inhaler according to the preamble of claim 1.

The present invention relates to an inhaler for delivery of a powder-form inhalation formulation from a blister strip with a plurality of blister pockets (also called blisters) containing the inhalation formulation in doses.

GB 2 407 042 A discloses an inhaler with a rolled-up blister strip. The inhaler comprises a manually operated, pivotable actuator, which operates a conveyor for stepwise moving the blister strip. The actuator supports a piercer and an associated mouthpiece. By pivoting the actuator, the blister strip and be moved forward and blister pockets of the blister strip can be pierced one after the other. When a patient breathes in an air stream passes through the previously pierced blister pocket, with the result that the inhalation formulation in the blister pocket mixes with the air and is discharged to the patient. Before use, a mouthpiece cover of the inhaler has to be opened. The mouthpiece cover can be pivoted around an axis that extends in a plane particular to the pivot axis of the actuator.

Re-closing of an opened blister is already known from U.S. Pat. No. 7,069,929 B2. The re-closing prevents undesired escape and distribution of the inhalation formulation within the inhaler.

Object of the present invention is to provide an inhaler with simple and/or compact construction and/or with optimized design, handling and/or functionality.

The above object is achieved by an inhaler according to claim 1. Advantageous embodiments are subject of the sub-claims.

According to present invention, a marking device is provided for marking the blister strip and/or blister pockets preferably within the inhaler and/or during use of the inhaler. This allows an optimized marking, in particular numbering.

Figure 2:
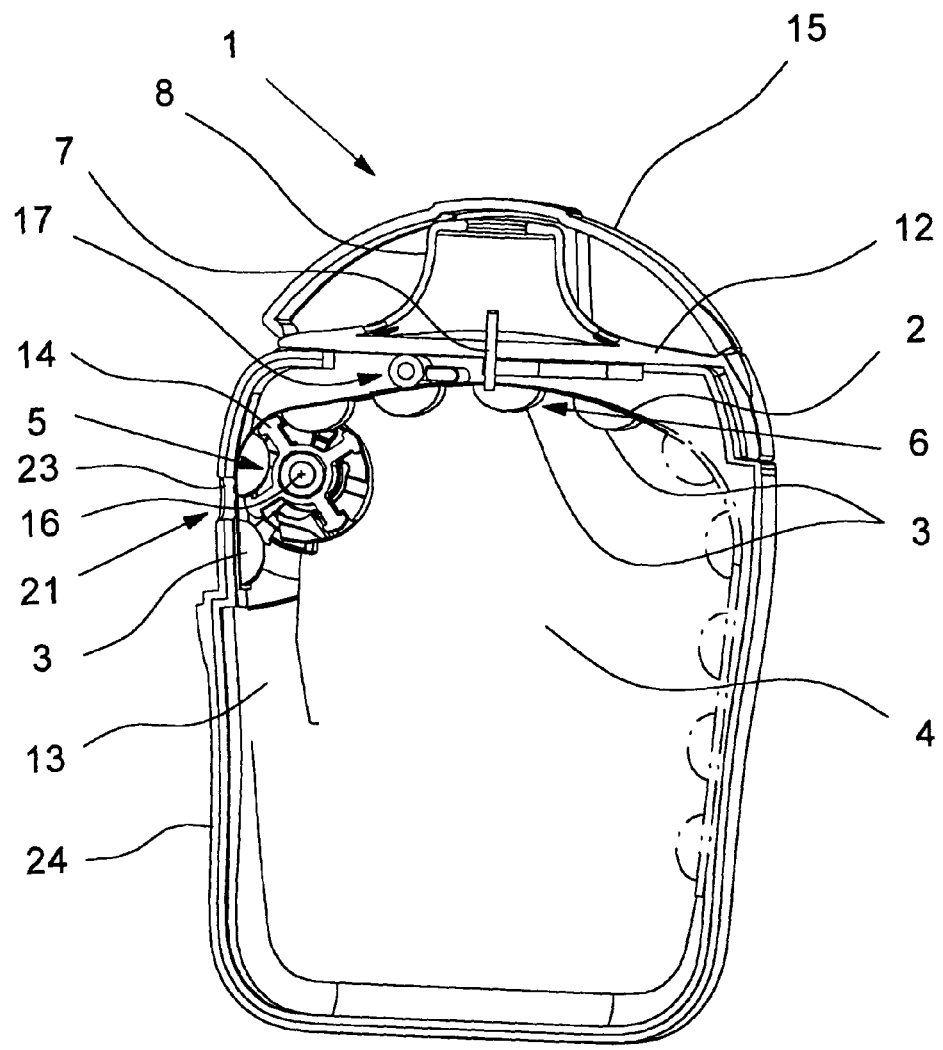
Figure 3:
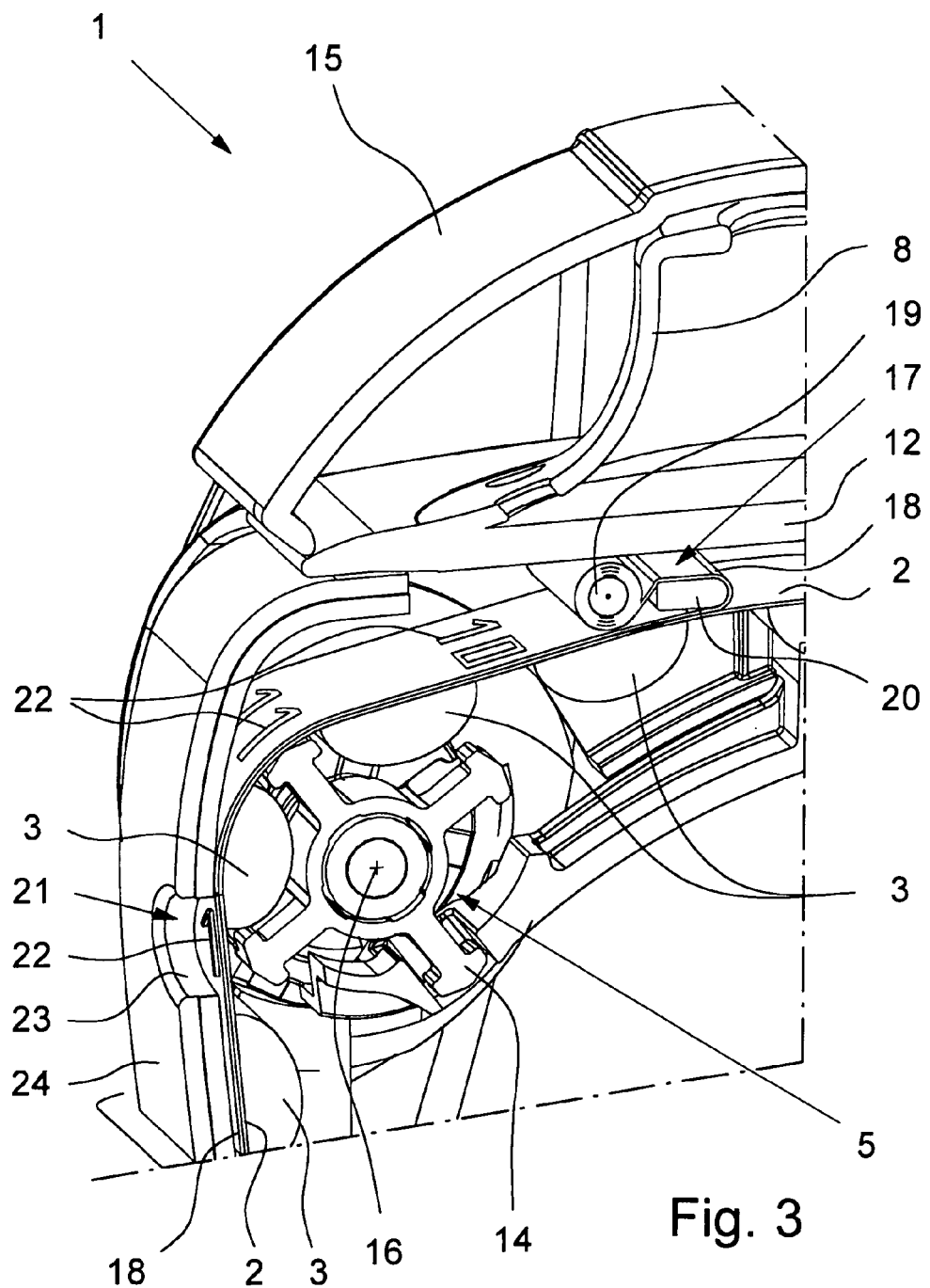
Figure 4:
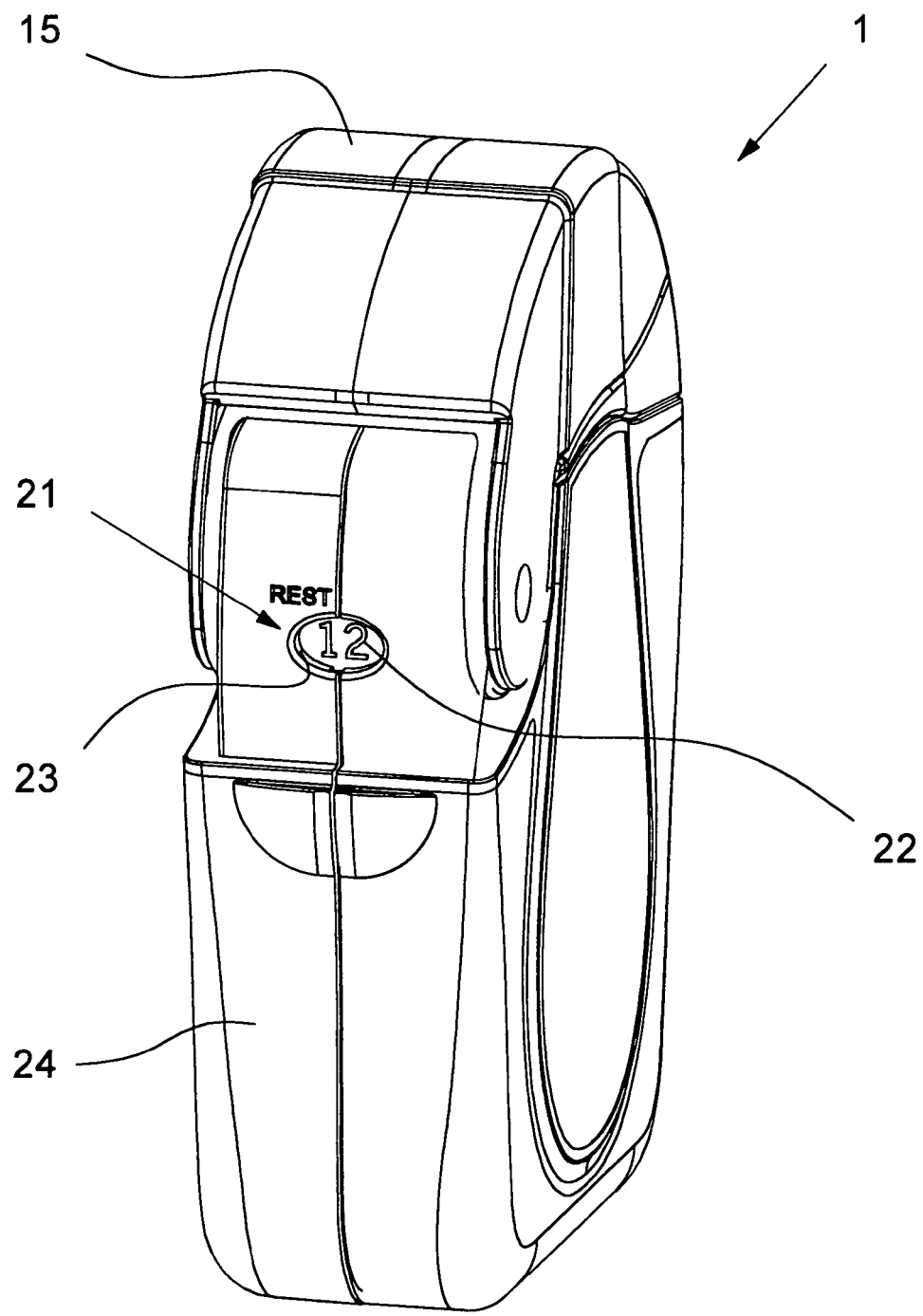

Further aspects, features, properties and advantages of the present invention are described in the claims and the subsequent description of a preferred embodiment, with reference to the drawing. There are shown in:

FIG. 1 a schematic sectional view of an inhaler without mouthpiece cover;

FIG. 2 a schematic sectional representation of the inhaler with closed mouthpiece cover; and FIG. 3 a partial, enlarged view of FIG. 2; and FIG. 4 a side view of the inhaler.

In the Figures, the same reference numbers are used for identical or similar parts, even if a repeated description is omitted. In particular identical or corresponding advantages and properties then also result or may be achieved.

FIG. 1 shows in a schematic sectional representation an inhaler 1.

The inhaler 1 serves to deliver a powdered inhalation formulation from a band-shaped blister strip 2. The blister strip 2 is finite, not forming an endless or closed loop. It has a large number of blister pockets 3 respectively containing directly a dose of the loose inhalation formulation. Thus, the formulation is pre-metered.

The inhaler 1 has a reservoir 4 for the still unused blister strip 2 with closed (sealed) blister pockets 3. The blister strip 3 is rolled up or wound up in the reservoir 4. In the representation example the reservoir 4 is formed such that the blister strip 2 can be moved outwards or pulled out of the reservoir 4 as easily as possible.

In the representation example the blister strip 2 is directly received in the reservoir 4. However, instead of this a cassette, a container, a drum or suchlike can also be fitted or inserted with the blister strip 2 into the inhaler 1 or the reservoir 4.

The inhaler 1 has a conveyor 5 for stepwise onward movement in direction of arrow 5a by one blister pocket 3 in each case, in order to feed the blister pockets 3 successively to an opening and/or removal position 6 where the respective blister pocket 3 is opened and can be emptied.

The blister pockets 3 can be opened respectively preferably by means of a piercing member 7, which punctures cuts open a lid of the respectively aligned blister pocket 3 in position 6. The piercing member 7 is hollow and in fluid connection with an adjacent mouthpiece 8 of the inhaler 1.

During or for inhalation a patient or user, not represented, places the mouthpiece 8 in his mouth and breathes in. The respectively opened blister pocket 3, into which the piercing member 7 extends, is thereby emptied by sucking in. An air stream 9 of ambient air is sucked in and passed through the opened blister pocket 3 such that the loose powder 10 (forming the inhalation formulation and being schematically shown in FIG. 1 only in the actually opened blister pocket 3 below mouthpiece 8) is dispensed with the sucked-in ambient air as an aerosol cloud 11 via the mouthpiece 8. This situation is schematically represented in FIG. 1.

The inhaler 1 has a preferably manually actuateable, lever-like actuator 12 being pivotally mounted to a housing of the inhaler 1.

The piercing member 7 and the mouthpiece 8 are attached to and supported by the actuator 12.

The actuator 12 is operable (pivotable) to cause the piercing member 7 to puncture the lid of the respectively aligned blister pocket 3 in position 6 below the mouthpiece 8.

When the actuator 12 swivels from the position shown in FIG. 1 (here anti-clockwise) to a partially opened position, the piercing member 7 is withdrawn from the last-pierced blister pocket 3.

Then, the blister strip 2 is moved forward one blister pocket 3, so that the next blister pocket 3 is moved in position 6. This will be explained in more detail later.

When the actuator 12 swivels back into the position shown in FIG. 1, i.e. is manually moved back, the next aligned blister pocket 3 of the blister strip 2 is punctured by the piercing member 7 and thereby opened. Then, the next inhalation can take place, i.e. the inhaler 1 is activated.

The inhaler 1 has a receiving space or apparatus 13 to receive or store the used part of the blister strip 2. The receiving space or apparatus 13 is preferably formed such that the used part can be wound up. FIG. 1 shows a situation with essentially filled reservoir 4 and still essentially empty receiving space 13.

The conveyor 5 comprises a conveying wheel 14, which can engage between the blister pockets 3 and thus convey the blister strip 2 in form-locking or form-fit manner. This allows very secure or precise moving or indexing of the blister strip 2 as desired and/or necessary.

The conveyor 5 or its conveying wheel 14 is arranged between the reservoir 4 and the receiving apparatus 13, in particular between the removal position 6 and the receiving apparatus 13, thus after the emptying of the blister pockets 3.

The pivot axis of the actuator 12 is coaxial with the rotation axis of the conveying wheel 14. In particular, the actuator 12 may be supported by an axle of the conveying wheel 14.

The inhaler 1 comprises a mouthpiece cover 15. The mouthpiece cover 15 is not shown in FIG. 1, which explains the basic principle of the inhaler 1, but in FIG. 2 which shows a more realistic, but still schematic sectional view of the inhaler 1. FIG. 2 shows the inhaler 1 with closed mouthpiece cover 15, wherein the blister strip 2 has been partly omitted for illustration purposes.

The mouthpiece cover 15 is pivotable around a cover axis 16, which is indicated in FIG. 2 and extends perpendicular to the drawing plane in the present representation.

The pivot axis of the actuator 12 extends coaxial to or with the cover axis 16. The rotation axis of the conveying wheel 14 extends coaxial to the cover axis 16 and to the pivot axis of the actuator 12.

The conveyor 5 or its conveying wheel 14 is driven by the mouthpiece cover 15, namely by the pivotal movement of the mouthpiece cover 15. In particular, the blister strip 2 is moved forward when the mouthpiece cover 15 is opened. Preferably, only part of the opening movement of the mouthpiece cover 15 actuates or operates the conveyor 5 or its conveying wheel 14 to move the blister strip 2 forward.

When the mouthpiece cover 15 is opened starting with the completely closed position shown in FIG. 2, in a first phase of the opening movement, for example up to a first angle of about 10, 20 or 30 degrees, the blister strip 2 is not moved due to a respective freewheel (not shown) between the mouthpiece cover 15 and the conveying wheel 14.

First of all, the actuator 12 has to be moved or opened in order to withdraw the piercing member 7 from the previously pierced and usually/already emptied blister pocket 3. This opening movement of the actuator 12 can be performed manually. However, the actuator preferably opens automatically together with the mouthpiece cover 15 or when the mouthpiece cover 15 reaches the first angle.

During the further opening (second phase) of the mouthpiece cover 15, the conveyor 5 or its conveying wheel 14 is actuated to move or index the blister strip 2 by one blister pocket 3 onward to the next blister pocket 3 that shall be emptied. This blister movement happens preferably up to the complete opening of the mouthpiece cover 15.

Only when the mouthpiece cover 15 is opened completely, i.e. reaches its end position, the movement of the blister strip 2 is set or fixed by a respective mechanism (not shown) and/or decoupled from the mouthpiece cover movement to keep the next blister pocket 3 in position 6 for puncturing. However, if the mouthpiece cover 15 is not fully opened and closed again, then the blister strip 2 is moved backward. This facilitates operation of the inhaler 1 and, in particular, prohibits that incomplete or intended operation of the mouthpiece cover 15 results in an undesired movement of the blister strip 2 and eventually in an undesired opening of the next blister pocket 3.

Preferably, a lock (not shown) is provided so that the opened actuator 12 can be closed again only if the mouthpiece cover 15 has been fully opened or has been or has been pivoted back the first angle or if the last-pierced pocket 3 has been moved back into position 6. Thus, the piercing member 7 cannot be pushed against an area of the blister strip 2 without or beside a blister pocket 3.

When the mouthpiece cover 15 has been fully opened and the next blister pocket has been moved in position 6, the actuator 12 can be pivoted back, i.e. closed, in order to pierce the already aligned, still closed blister pocket 3. Then, the inhaler 1 is ready for inhalation, i.e. activated as already described.

After inhalation, the inhaler 1 can be closed by pivoting back the mouthpiece cover 15 into its closed position.

In order to operate the conveyor 5 or its conveying wheel 14 by movement of the mouthpiece cover 15 as described above or in any other suitable manner, the mouthpiece cover 15 is coupled with the conveyor 5, in particular the conveying wheel 14, via the already mentioned freewheel and/or via a suitable transmission, a slipping clutch or any other suitable coupling.

Preferably, the freewheel, transmission, coupling or the like is integrated into or located adjacent to the conveying wheel 14 or a respective axle.

The inhaler 1 comprises preferably a preferably marking device 17 (shown in FIG. 2 and in the enlarged partial view according to FIG. 3) for marking, preferably numbering, the blister strip 2 and/or blister pockets 3, in particular for marking the blister strip 2 and/or blister pockets 3 within the inhaler 1 and/or during use of the inhaler 1.

In the present embodiment, the inhaler 1 or marking device 17 uses a marked means preferably for permanent fixture onto the blister strip 2 for marking the blister strip 2 and/or blister pockets 3. Preferably, the marked means is band-like and/or a tape 18 or the like. In the following, the description focuses on the tape 18 as preferred means. However, any other suitable means for marking can be used.

The means is preferably permanently fixed, in particular adhered onto the blister strip 2. In the present embodiment, the means/tape 18 is preferably self-adhesive. Alternatively or additionally, the blister strip 2 could also be self-adhesive, in particular at least partially and/or after opening of blister pockets 3, e.g. by removing of a cover foil or the like.

The tape 18 is preferably wound up in the inhaler 1 before use. In particular, the inhaler 1 or marking device 17 comprises a spool 19 for or with the tape 18.

In one embodiment, the inhaler 1 or the marking device 17 comprises a guiding element, in particular a deflector 20 of the like, for guiding or pressing the means/tape 18 onto the blister strip 2. In the shown embodiment, the guiding element or deflector 20 is stationary. However, the guiding element could be moveable or flexible or rotatable, e.g. a roll or the like.

The advantage of the guiding element is that the inclination or contact angle, with which the tape 18 is supplied to the blister strip 2, is constant independently on the diameter on spool 19.

Preferably, any guiding element is not provided. This facilitates the construction and operation of the inhaler 1.

Preferably, the tape 18 has the width as the blister strip 2. This facilitates guidance.

Preferably, the beginning of the tape 18 is initially connected with the free end or front end of the blister strip 2. This ensures that the blister strip 2 and the tape 18 are jointly moved forward when the conveyor 5 is operated.

In particular, the tape 18 is moved or drawn from the spool 19 by means of the blister strip movement or alternatively directly by respective driving by the conveyor 5. However, the tape 18 could also be moved or drawn from the spool 19 by a separate drive. In particular, the spool 19 could be driven.

The marking device 17 or guiding element is preferably located after the opening and/or removal position 6 or piercing member 7 and/or is located preferably before the conveyor 5 or conveying wheel 14.

In the present embodiment, the means/tape 18 is preferably in one-piece-form. However, it could also consist of multiple parts or pieces or could be separated into multiple parts or pieces, in particular wherein the multiple parts or pieces can be respectively associated to one blister pocket 3 or a group of blister pockets 3.

The inhaler 1 preferably comprises a display device 21 for displaying marks or numbers 22 associated to the blister pockets. In particular, the display device 21 shows or counts the number of already used or of still useable blister pockets 3 and, thus, doses of formulation.

In the present embodiment, the display device 21 allows marking of the blister strip and/or blister pockets 3 with numbers 22 as shown in FIG. 3.

The numbers 22 can be displayed or seen preferably through a window 23 of the display device 21 in a housing 24 of the inhaler 1 in the preferred embodiment as shown in FIG. 3 and FIG. 4.

Preferably, the marking device 17 comprises the display device 21 and/or uses the tape 18 for marking or numbering the blister strip 2 and/or blister pockets 3.

In particular, the means/tape 18 is used for marking and/or numbering the blister 2 and/or blister pockets 3 as desired. In particular, the tape 18 is provided with the respective numbers 22.

Preferably, the tape 18 is connected at only one portion and/or its free end with the free end or beginning or any other suitable portion of the blister strip 2. This does not only facilitate joint or simultaneous movement of the blister strip 2 and tape 18, but does ensure also a correct positioning or initialization of the numbers 22 to the blister pockets 3 so that the numbers 22 will be visible one after the other through window 23 and/or will correctly correlate to the blister pockets 3.

In the present embodiment, the numbers 22 are preferably printed on the tape 18. However, it is also possible to place the numbers 22 in any other suitable form or method onto the tape 18 or directly on the blister strip 2, in particular on the opened blister pockets 3.

According to a further aspect of the present invention, which may also be realized independently, the numbers 22 or any other marks may additionally or alternatively be formed by or comprise protrusions, elevations or the like so that blind people can recognize the numbers 22 or marks by touching. Then, the inhaler 1 comprises an open window 23 or any other suitable opening in the housing 24 of the inhaler 1 and/or a flexible housing portion to allow the desired feeling of the marks, numbers, elevations, protrusions or the like. Preferably, the window 23 or opening is covered by a transparent, soft and/or flexible film, foil, membrane or the like to hermetically close the window 23 or opening, but to allow the mentioned feeling of the elevations, protrusions or the like in particular by blind people.

According to another aspect of the present invention, which can also be realized independently, the marks or numbers 22 are preferably located or formed on the back or flat side of the blister strip 2 and/or on the side of opening the blister strip 2, in particular in the area where the blister pockets 3 are opened and/or where a foil or the like closes the blister pockets 3.

The blister pockets 3 can be provided with relatively large numbers 22 (in particular the complete area of the opened side of the blister pocket 3 and/or the complete width of the blister strip 2 can be used).

Preferably, the numbers 22 indicate the rest of blister pockets 3 which can still be used, i.e. the total number of the remaining possible uses or inhalations or the total number of already used blister pockets 3.

Preferably, the inhaler 1 is portable, works only mechanically and/or is hand-held.

Preferably, the terms "blister strip" and "blister pockets" have to be understood in a very broad sense to cover also other kinds of storage means with receptacles or even bulk storages for the formulation.

LIST OF REFERENCE NUMBERS 1 inhaler
2 blister strip
3 blister pocket
4 reservoir
5 conveyor
5a onward movement
6 opening and/or removal position
7 piercing member
8 mouthpiece
9 air stream
10 powder
11 aerosol cloud
12 actuator
13 receiving apparatus
14 conveying wheel
15 mouthpiece cover
16 cover axis
17 marking device
18 tape
19 spool
20 guiding element
21 display device
22 number
23 window
24 housing

The invention claimed is:

1. In an inhaler (1) for delivery of an inhalation formulation from a band-shaped blister strip (2) with a plurality of blister pockets (3) containing the inhalation formulation in doses, comprising a piercing member (7) to puncture a lid of an aligned blister pocket (3), the inhaler (1) being designed such that by breathing in during inhalation an air stream (9) of ambient air can be sucked or delivered in order to discharge the respective dose from an opened blister pocket (3) and to deliver the dose with the ambient air as an aerosol cloud (11), the improvement which is characterized by the inhaler (1) comprising a marking device (17) for marking the blister strip (2) or blister pockets (3) where the marking device (17) comprises a marking means (18) for fixture onto the blister strip (2) wherein the marking means (18) comprises multiple parts or pieces or can be separated into multiple parts or pieces, in particular the multiple parts or pieces being respectively associated to one blister pocket (3) or a group of blister pockets (3).

2. The inhaler as recited in claim 1 characterized in that the marking device (17) further comprises a guiding element including a deflector (20) for guiding or pressing the marking means (18) onto the blister strip (2).

* * * * *

UNITED STATES PATENT AND TRADEMARK OFFICE
CERTIFICATE OF CORRECTION

PATENT NO.         : 8,596,267 B2                                       Page 1 of 1
APPLICATION NO.    : 12/863488
DATED              : December 3, 2013
INVENTOR(S)        : Thoemmes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 322 days.

Signed and Sealed this
Twenty-second Day of September, 2015

Michelle K. Lee
*Director of the United States Patent and Trademark Office*